United States Patent [19]

Levine

[11] Patent Number: 5,226,411
[45] Date of Patent: Jul. 13, 1993

[54] AEROSOL NEBULIZER HEATER

[76] Inventor: Walter Levine, 6948 N. Keating, Lincolnwood, Ill. 60646

[21] Appl. No.: 874,679

[22] Filed: Apr. 27, 1992

Related U.S. Application Data

[63] Continuation-in-part of Ser. No. 666,055, Mar. 7, 1991, abandoned.

[51] Int. Cl.⁵ ............................................. A61M 16/00
[52] U.S. Cl. ........................ 128/203.26; 128/203.27; 128/204.17
[58] Field of Search .................. 128/200.14, 200.16, 128/203.12, 203.17, 203.26, 204.17, 203.27

[56] References Cited

U.S. PATENT DOCUMENTS

| | | | |
|---|---|---|---|
| 3,903,883 | 9/1975 | Pecina et al. | 128/200.21 |
| 4,305,388 | 12/1981 | Brisson | 128/204.17 |
| 4,564,748 | 1/1986 | Gupton | 219/497 |
| 4,587,966 | 5/1986 | Albarda | 128/202.22 |
| 4,676,237 | 6/1987 | Wood et al. | 128/203.17 |
| 4,819,625 | 4/1989 | Howe | 128/200.18 |
| 4,911,157 | 3/1990 | Miller | 128/200.21 |
| 4,951,659 | 8/1990 | Weiler et al. | 128/200.18 |
| 5,063,921 | 11/1991 | Howe | 128/200.14 |

Primary Examiner—Edgar S. Burr
Assistant Examiner—Aaron J. Lewis
Attorney, Agent, or Firm—Welsh & Katz, Ltd.

[57] ABSTRACT

An aerosol nebulizer heater includes a housing with an inlet end for operational engagement with a nebulizer for the receipt of pressurized aerosol, a device for heating the aerosol, and a system for monitoring and controlling the temperature of the heated aerosol as the aerosol is passed through the housing and toward a patient, so that the patient receives the heated aerosol at a relatively constant temperature.

24 Claims, 4 Drawing Sheets

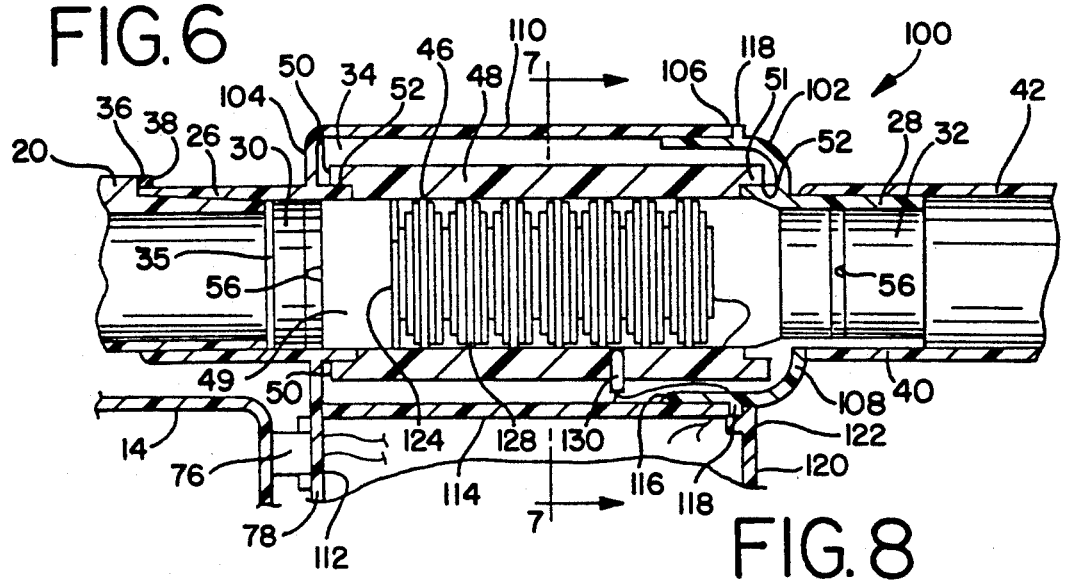
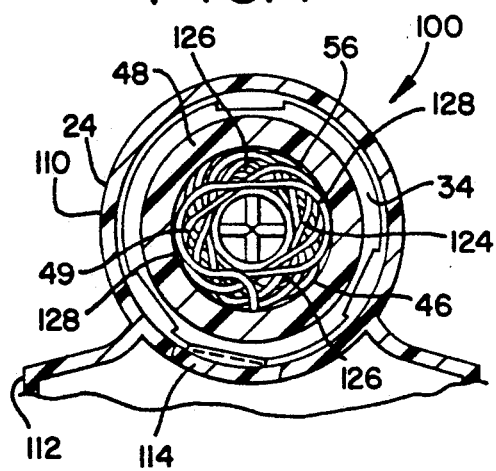
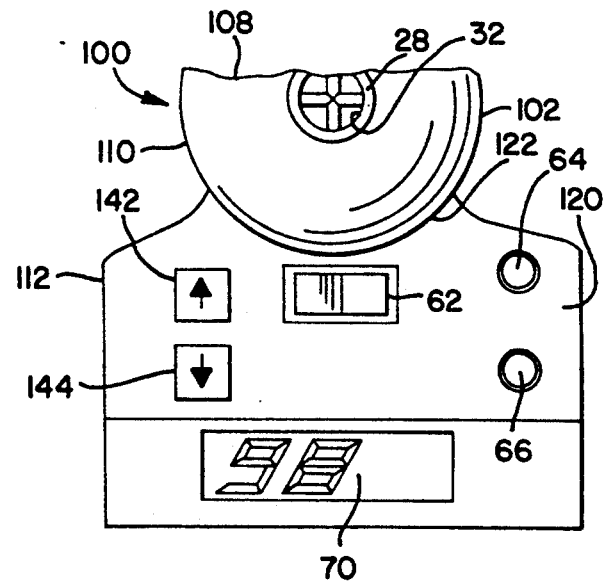
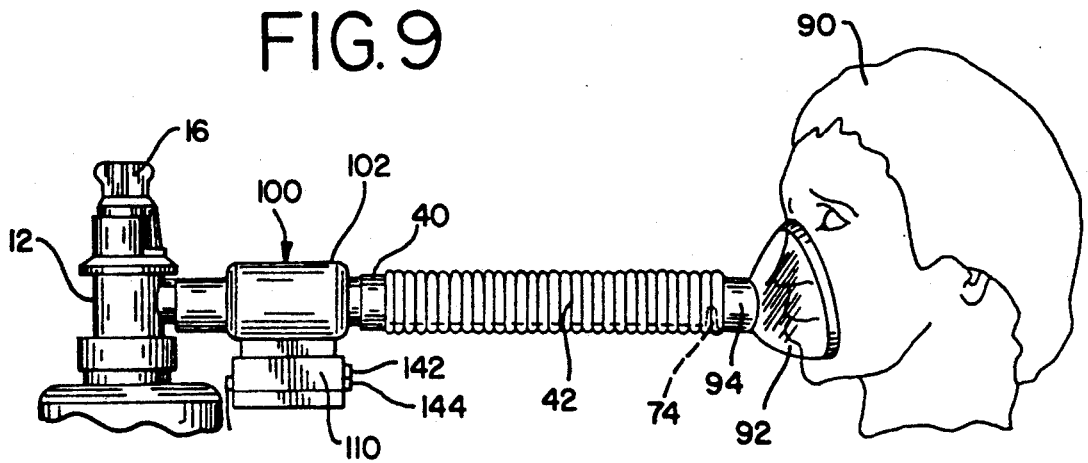

AEROSOL NEBULIZER HEATER

RELATED APPLICATION

This application is a continuation-in-part of Ser. No. 07/666,055 filed Mar. 7, 1991 now abandoned and entitled "Aerosol Nebulizer Heater."

BACKGROUND OF THE INVENTION

The present invention relates to respiratory care devices, and specifically to a heater for use with respiratory nebulizers which produce an aerosol to be delivered to the patient.

In conventional respiratory care systems including nebulizers, oxygen is mixed with a liquid, usually sterile water, saline solution or other respiratory solution to form an aerosol which is passed through a flexible feed tube and ultimately delivered to the patient through a face mask. A recent trend in respiratory therapy is to provide a heated aerosol to the patient to minimize stress on the patient's respiratory system.

Conventional nebulizer heaters have concentrated on heating the supply of sterilized water prior to the nebulization process. However, a significant drawback to this approach is that the water loses heat in the nebulization process. In addition, the tube through which the aerosol passes to reach the patient is usually cooler than the temperature of the heated water. Consequently, as the heated aerosol progresses through the tube, condensation appears on the inside of the tube. As the treatment continues, the tube eventually fills with condensate water, prematurely cooling the aerosol and wasting heat. Attempts to heat the tube instead of the water have been abandoned as being ineffective or impractical.

Another unsolved design parameter of nebulizer heaters is that when heat is cyclically applied to the aerosol, a so-called "spike effect" results, in which excessive heat is applied to achieve a target temperature, but instead exceeds the target due to the cumulative effect of the applied heat. The control circuitry then responds by reading the higher temperature and shutting off the heat, thus causing the temperature of the aerosol to prematurely plummet.

In addressing the above-identified drawbacks of conventional nebulizer heater systems, an important design parameter to be considered is that if too much heat is applied to an aerosol, the moisture content will decrease to the point that the aerosol's therapeutic benefits are neutralized. Accordingly, enough heat must be applied to prevent condensation and to provide the patient with an adequately heated aerosol, while avoiding overheating the aerosol to the point of desiccating it.

Another important design factor is that any heat applied must be accurately monitored to maintain a constant temperature of the aerosol reaching the patient, and to avoid spiking.

Thus, there is a need for a nebulizer heater which delivers heated aerosol to the patient within a specified temperature range to provide the therapeutic benefits of heated aerosols. There is a further need for a nebulizer heater which accurately monitors the aerosol temperature at the point the patient receives the aerosol, and which adjusts the aerosol temperature in a manner which avoids spiking. There is also a need for such a nebulizer heater which can be readily adapted to existing nebulizer systems for accurate, safe and energy efficient operation.

SUMMARY OF THE INVENTION

Accordingly, the present nebulizer heater addresses the above-identified drawbacks of conventional systems by heating the aerosol after it leaves the nebulizer. In addition, the present heater is provided with a temperature control system which is calibrated to both account for heat loss in the aerosol transfer tube, and minimize the loss of aerosol moisture content. The temperature control system includes a safety temperature feedback feature for monitoring the temperature of the aerosol as it leaves the heater. Monitoring may also occur at the point of aerosol reception by the patient.

More specifically, a heater is provided for use with a respiratory nebulizer producing a pressurized aerosol, including a housing having an inlet end and an outlet end, each of the ends having a respective port. The inlet end port and the outlet end port are in fluid communication with each other. The inlet end port is configured for fluid communication with the nebulizer to receive the aerosol upon connection of the housing to the nebulizer. Also included is a device for heating the aerosol as the aerosol passes through the housing and out the outlet end port, the heating device having a tubular heating chamber including a tubular heating element with multiple heated surfaces disposed in the chamber so that aerosol passing through the chamber directly contacts the heated surfaces.

In addition, the heater has an aerosol temperature control system including a temperature monitor located adjacent the outlet port and connected to the heater so as to provide feedback information to a temperature controller. In this manner, the heater cycles to heat only when necessary, and thus operates more efficiently. Furthermore, the control system is calibrated so that the aerosol is only heated to the extent necessary to provide the patient with a correctly heated aerosol having a sufficient moisture content. If desired, a temperature sensor may be positioned adjacent the point where the patient receives the aerosol in order to more closely monitor aerosol temperature.

The present heater also includes at least one safety device for preventing the overheating of the heating element, for notifying health care personnel of a heater failure, and for preventing the operation of the heater if the unit is improperly attached to the nebulizer.

BRIEF DESCRIPTION OF THE DRAWINGS

FIG. 1 is a front perspective elevational view of the present nebulizer heater shown connected to a nebulizer;

FIG. 2 is a sectional view taken along the line 2—2 of FIG. 1 and in the direction generally indicated;

FIG. 3 is a sectional view taken along the line 3—3 of FIG. 2 and in the direction generally indicated;

FIG. 4 is a schematic diagram of the electronic circuit used to operate the heater of FIG. 1;

FIG. 5 is a diagrammatic representation of a respiratory nebulizer system shown connected to a patient and employing the present nebulizer heater;

FIG. 6 is a vertical sectional view of an alternate embodiment of the nebulizer heater of the invention;

FIG. 7 is a sectional view taken along the line 7—7 of FIG. 6 and in the direction generally indicated;

FIG. 8 is a fragmentary front elevational view of the nebulizer heater illustrated in FIG. 6;

FIG. 9 is a diagrammatic representation of a respiratory nebulizer system shown connected to a patient and employing the nebulizer heater of FIG. 6; and FIG. 10 is a schematic diagram of the electronic circuit used to operate the heater of FIG. 6.

DESCRIPTION OF THE PREFERRED EMBODIMENT

Figure 1:
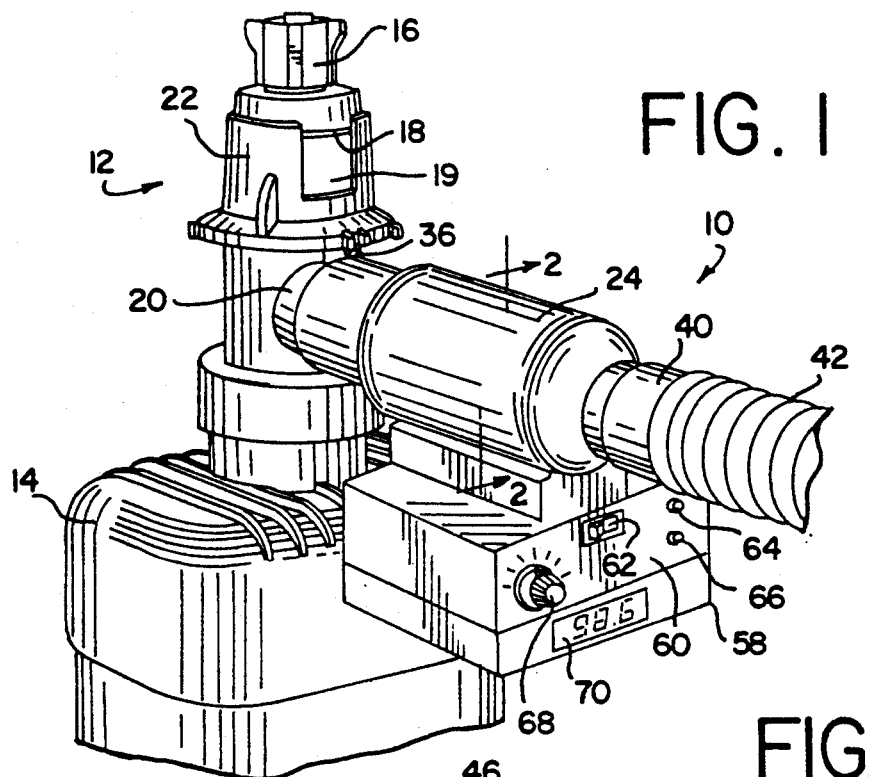

Referring now to FIG. 1, the nebulizer heater of the invention is indicated generally at 10. The heater 10 is shown connected to a conventional nebulizer indicated generally at 12. The nebulizer 12 includes a container 14 for a supply of sterile water or other therapeutic liquid, an axially rotatable coupler 16 for a conventional oxygen flow meter which delivers pressurized oxygen, and a mixing chamber 18 into which liquid from the container 14 is drawn via a Venturi effect.

Once in the chamber 18, the liquid is mixed with oxygen introduced through the coupler 16 and also with air entering through an adjustable opening 19 to form an aerosol mist, and is forced under pressure through a tubular outlet 20 as is known in the art. The nebulizer 12 is preferably equipped with an axially rotatable collar 22 for controlling the amount of air entering the chamber 18 through the opening 19. This air is used to dilute the oxygen to form a therapeutically beneficial aerosol. It will be understood that the container 14, the coupler 16, the mixing chamber 18 and the outlet 20 are in fluid communication with each other.

Figure 2:
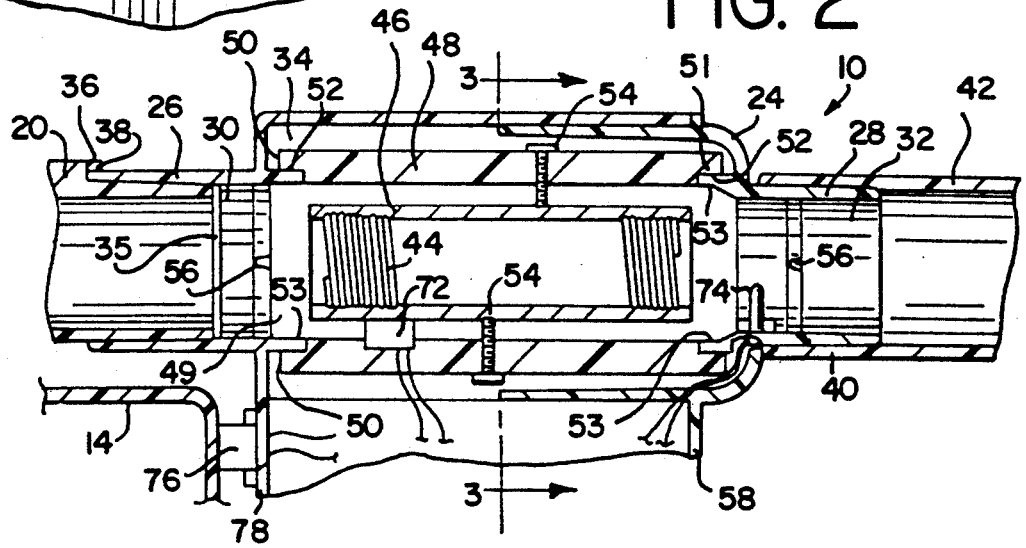
Figure 3:
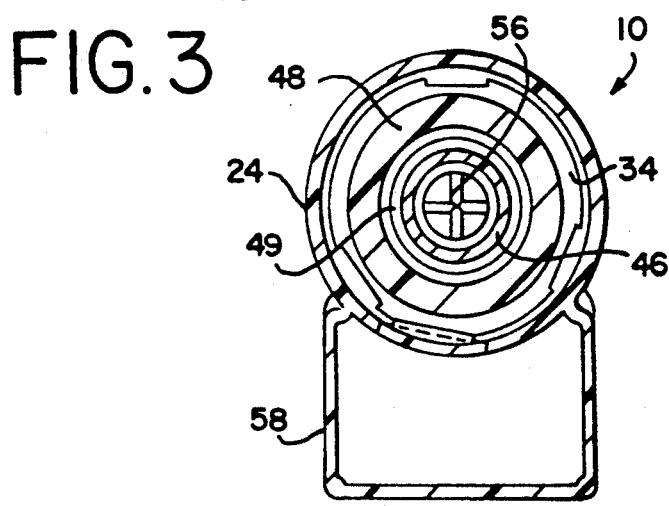

Referring now to FIGS. 1-3, the nebulizer heater 10 is provided with an outer housing 24, which in the preferred embodiment is manufactured of high impact plastic. The housing 24 has an inlet end 26 and an outlet end 28, the inlet end having a port 30 and the outlet end having a port 32. The two ports 30, 32 are separated by a central chamber 34 and are in fluid communication with each other through the chamber.

The inlet end port 30 is dimensioned to slide over the nebulizer outlet 20 with a friction fit, and may include an inner shoulder 35 which serves as a stop for the nebulizer outlet. This is the major connection point between the nebulizer heater 10 and the nebulizer 12. As such, the engagement between the inlet port 30 and the nebulizer outlet 20 must be secure, and must also position the heater 10 accurately relative to the nebulizer 12. In cases where the nebulizer outlet 20 has an upwardly projecting mounting lug 36, the inlet end port 30 is preferably provided with a locating notch 38 to properly position the heater 10 upon the nebulizer 12 in interlocking relationship. The notch 38 acts as a keyway to mechanically maintain a vertical position of the heater 10 without a separate locking mechanism. The outlet end port 32 is dimensioned to slidingly accommodate an end 40 of a length of respiratory tubing 42, which is shown as being of the corrugated type.

The central chamber 34 of the housing 24 encloses a heating element 44, which in the preferred embodiment is an elongate heating coil made of Enconal-type shielded wire. The coil 44 is centrally located within the chamber 34 and is preferably coaxial with the ports 30, 32. A tubular heat sink 46, preferably made of stainless steel, surrounds the coil 44, and a cylindrical insulator barrel 48 defines a heating chamber 49 around the heat sink 46 and within the chamber 34.

The barrel 48 is preferably manufactured of TEFLON or other heat resistant material, and is dimensioned so that the chamber 49 has a diameter which generally corresponds to the diameter of the inlet and outlet end ports 30, 32. The respective ends 50, 51 of the barrel 48 each have a peripheral recess 52 on inner edges thereof which is configured to sealingly engage an inwardly projecting annular flange 53 located at each end of the chamber 49. In this manner, heat is retained within the chamber 49 and the housing 24 is protected from overheating.

A pair of diametrically opposed stainless steel screws 54 pass through the insulating barrel 48 into the heat sink 46 to secure the heat sink 46 in position relative to the barrel as well as to the chamber 49. A safety crossbar 56 is fixed to the housing 24 at each end of the chamber 49 to prevent individuals from contacting the coil 44, the heat sink 46, or the barrel 48.

Referring now to FIG. 1, the nebulizer heater 10 further includes a control module 58 integrally joined to a lower portion of the housing 24. The module 58 is provided with a small control panel 60 which includes an on/off power switch 62, a power indicator light 64, a heater indicator light 66, and the control actuator portion of a potentiometer 68 calibrated for a specified temperature range. If desired, the control panel 60 may include a digital temperature display 70.

Referring now to FIG. 2, associated with the control module 58 is a thermostat 72 mounted in close, operational proximity to the heat sink 46, and which is designed to cut the flow of current to the coil 44 when the temperature reaches approximately 130° F. In this manner, the heater 10 is prevented from overheating, and the patient is assured of receiving properly heated aerosol having a sufficient moisture content.

In addition, the heater 10 has a thermistor 74 disposed in the outlet end port 32 to measure the temperature of the aerosol as it leaves the heating chamber 49. In the preferred embodiment, the thermistor 74 is capable of measuring temperatures in the range of 115°-120° F.

In order to prevent the operation of the heater 10 when it is improperly connected to the nebulizer 12, the control module 58 is provided with a push button-type momentary safety switch 76 on a rear side 78 of the module. The switch 76 is positioned upon the heater 10 to contact and be depressed by the container 14 when the heater is properly connected to the nebulizer 12. If an improper or inadequate connection is made, the switch 76 will not be depressed, and current will not be allowed to flow through the coil 44.

Figure 4:
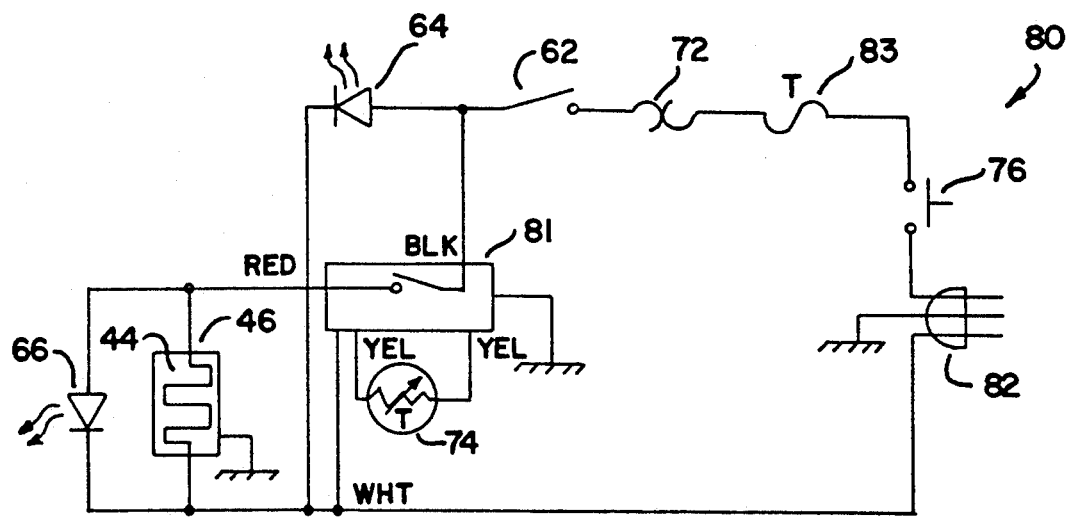

Referring now to FIG. 4, a schematic representation is provided of the heater control circuit 80 used in the control module 58 to operate the heater 10. The heater control circuit 80 includes the power switch 62, the power indicator light 64, e.g. an L.E.D., the heating coil 44, a temperature controller 81, the heater indicator light 66, e.g. an L.E.D., the thermostat 72, the safety switch 76, a thermal fuse 83, and an aerosol temperature sensing device, here the thermistor 74.

A power plug 82, connected to a typical 120 VAC or possibly a 220 VAC power line from a wall socket, provides electric power to the heater control circuit 80. The line terminal of the 120 VAC line provides power through the safety switch 76, the thermal fuse 83, the thermostat 72, and the power switch 62, to the temperature controller 81 and the power indicator light 64. The neutral terminal of the 120 VAC power plug 82 connects to one end of the heating coil 44, the heater indicator light 66, the power indicator light 64, and the temperature controller 81. The earth ground terminal of the 120 VAC power plug 82 couples to the case of the temperature controller 81 and the heat sink 46 surrounding the heating coil 44. The output line of the temperature controller 81 connects both to the heater indicator light 66 and the other end of the coil 44. Finally, one sensing line of the temperature controller 81 couples to a first end of the thermistor 74. A second sensing line couples to a second end of the thermistor 74.

It will be evident that the power switch 62 and the safety switch 76 are connected in series through the thermostat 72 so that both must be activated before the coil 44 will receive power via the temperature controller 81. The power indicator light 64 indicates when the power is on, but not whether or not the coil 44 is receiving current.

The temperature controller 81 is selected to be of the type of AC proportional temperature controller Model 5C1-40 available from Oven Industries, Inc. located in Mechanicsburg, Pa., 17055, but may be any suitable current or voltage controller, which will provide adjustment of power to heat the coil 44 in the range of 115°–120° F. This is the optimum temperature of the aerosol as it leaves the outlet end port 32, and is set relatively high to accommodate heat loss which has been found to occur along a four to six foot length of respiratory tubing 42 (best seen in FIG. 5). The temperature controller 81 may accommodate a load current of up to 3 amperes. If a 220 VAC power source is used instead of a 120 VAC, the temperature controller may be of the type Model 5C1-46 also available from Oven Industries, Inc.

Power to the coil 44 is controlled by the temperature controller 81 through adjustment of the potentiometer 68 which is an internal component of the temperature controller. The heater indicator light 66 will be illuminated only when the coil is being heated. The power indicator light 64 and the heater indicator light 66 are L.E.D.s of the Archer brand type, part numbers in the 272-700 series, and are available from Radio Shack. However, any other suitable light sources may also be used. These L.E.D.'s 64, 66 contain resistive elements (not shown) to limit current flow through the L.E.D.'s. The thermal fuse 83 interposed between the safety switch 76 and the thermostat 72 will prevent power from being applied to the circuit when the temperature in the thermal fuse exceeds approximately 243° F. The thermal fuse is a thermal cut-off type, Model D115, available from Elmwood Sensors Inc., Pawtucket, R.I.

The thermistor 74 is disposed in the outlet end port 32 to measure the temperature of the aerosol as it leaves the heater 10. When the thermistor 74 senses temperatures exceeding 120° F., the temperature controller 81 reduces power to the coil 44 until the temperature falls within the desired range, whereafter the temperature controller again provides power to the coil 44.

The thermostat 72 is set so that the temperature around the heat sink 46 will not exceed 130° F. If the temperature reaches that limit, the thermostat 72 will interrupt current flow the coil 44.

Figure 5:
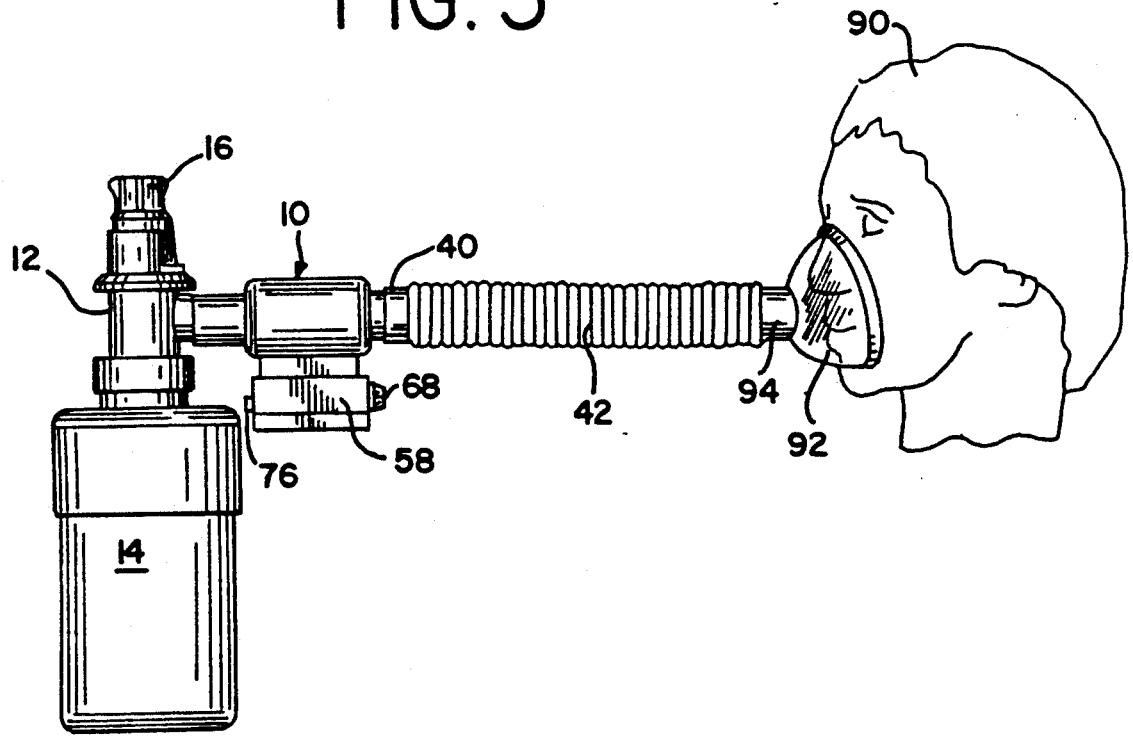
Figure 10:
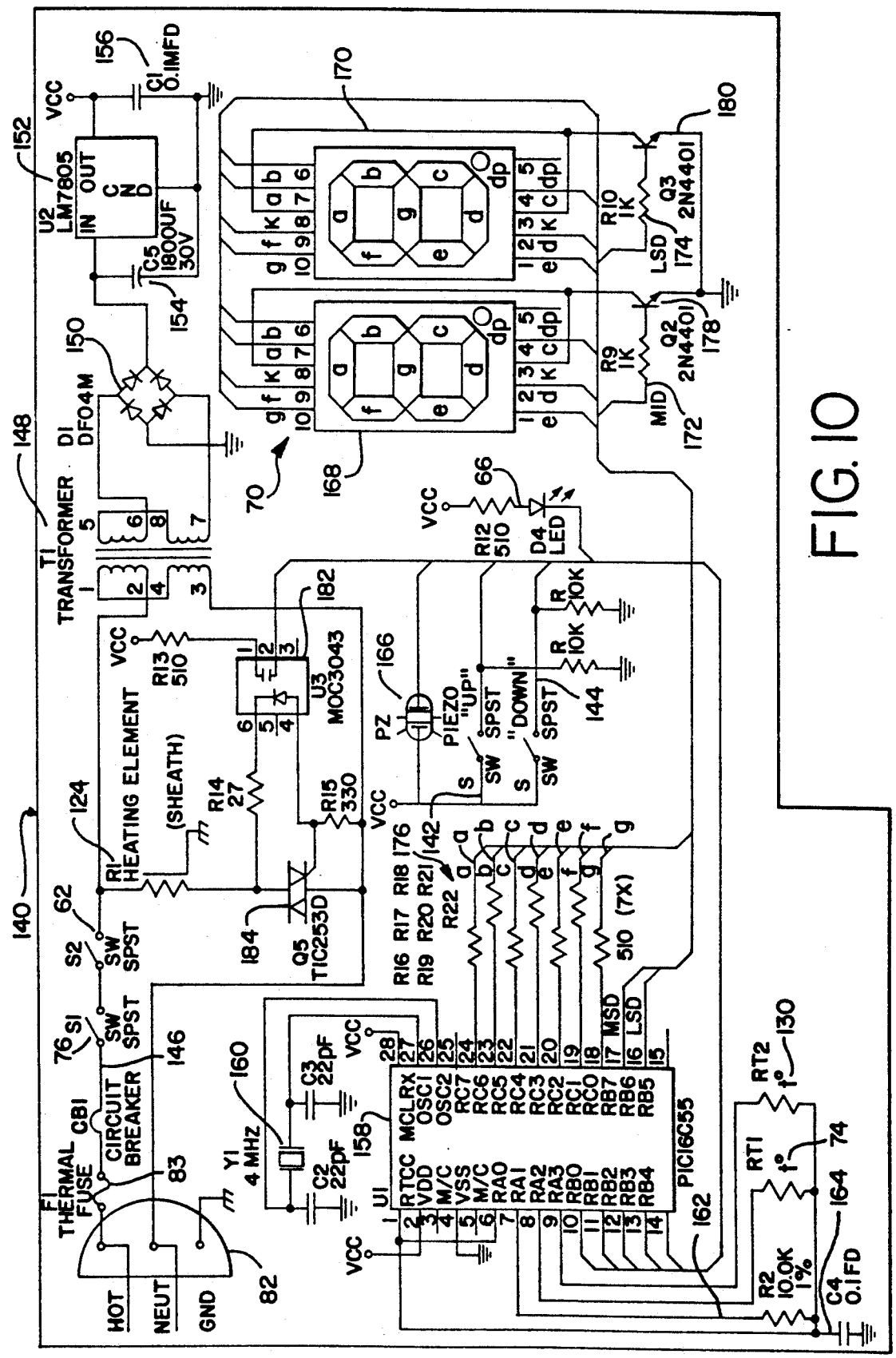

Referring now to FIG. 5, test results of the heater 10 of the invention have shown that with a tube 42 of a length in the range of four to six feet, and with the temperature of the aerosol leaving the outlet end port 32 of 115° to 120° F., a patient 90 wearing a face mask 92 connected to the end 94 of the tube 42 opposite the end 40 will receive an aerosol having a temperature in the range of 94°±3° F. This is an acceptable temperature range for therapeutic purposes, and the patient receives an aerosol which is not desiccated.

In operation, the heater 10 is operationally engaged with the nebulizer 12 so that the inlet end 26 matingly engages the nebulizer outlet 20, and the safety switch 76 is depressed against the container 14. Once the power cord is plugged in a conventional wall outlet (not shown), the power switch 62 is actuated, and the indicator light 64 is illuminated. Next, the potentiometer 68 is set at a desired temperature, depending on the length of the tube 42.

Oxygen and air are mixed with water from the container 14 in the nebulizer 12 to form an aerosol which is forced through the outlet 20 into the inlet port 30 of the nebulizer heater 10. The aerosol is forced into the heating chamber 49, where the temperatures of the heating coil 44 and the heat sink 46 are monitored by the thermostat 72. If the temperature rises too high, the thermostat cuts current flow to the coil 44, and the indicator light 66 goes out, alerting medical personnel that the heater is temporarily not heating.

The aerosol becomes heated in the chamber 49 and is forced through the outlet port 32, where the thermistor 74 measures its temperature. If the temperature of the aerosol is outside the previously specified limits, the thermistor 74 acts through the potentiometer 68 to control the coil 44.

Referring now to FIGS. 6–10, an alternate embodiment of the present nebulizer heater 10 is indicated generally at 100. Those components of the heater 100 which are identical to those of the heater 10 have been designated with identical reference numerals. Externally, the heater 100 is quite similar to the heater 10, and is connected between the nebulizer 12 and the respiratory tubing 42 in the same manner (best seen in FIG. 9).

To facilitate assembly, a housing 102 includes a closed end 104, shown on the left in FIG. 6, and an open end 106, shown on the right in FIG. 6. A heating chamber end plate 108 is dimensioned to enclose the upper portion 110 of the housing, which is separated from the lower portion 112 (shown partially) by a dividing wall 114. The heating chamber end plate 108 has a reduced inner peripheral edge 116 which frictionally engages and nests within the open upper portion 110.

End plate 108 also includes a radially extending lip 118 which abuts the edge of the open end 106. A lower end plate 120 encloses the lower portion 112 of the housing 102 and includes an upper edge 122 which overlaps the radially extending lip 118 to more securely retain the upper end plate 108 upon the housing 102, and to prevent moisture from entering the lower portion 112 from the upper portion 110. Basically, the upper portion 110 encloses the central chamber 34, and the lower portion 112 encloses the electronic components which operate and monitor the performance of the heater 100. To further seal the upper portion 110 against moisture leakage, a coating of silicone or other sealant may be applied liberally around the inside surface of the upper portion of the housing 102, and at the contact point of the end plate 108 with the open end 106.

Inside the central chamber 34 is found the cylindrical insulator barrel 48, which defines the heating chamber 49. Instead of the coil 44 and the tubular heat sink 46 of the heater 10, the heater 100 includes a heating element in the form of a "braided" coil 124. The coil 124 is basically tubular in shape, with each winding of preferably Enconal coated wire having a slightly different diameter than the next adjacent winding, as seen in FIG. 6. The result of this winding arrangement is that the coil 124 assumes a "braided" or "basket weave"

appearance as seen from the end or in section (best seen in FIG. 7), wherein substantially the entire surface area of the windings forming the coil is exposed to the flow of aerosol passing through the chamber 49. Also, aerosol may pass through openings 126 created by the winding pattern of the coil 124. The coil 124 is frictionally secured within the cylindrical insulator barrel 48, preferably by the largest diameter windings 128.

Another difference between the heater 10 and the heater 100 is that the thermostat 72 has been replaced by a second thermistor 130, which contacts the coil 124 through an opening 132 in the barrel 48. The second thermistor 130 is used to monitor the temperature of the coil 124.

Also, the first thermistor 74 has been moved from its prior position in the outlet end port 32, to a new location at the end 94 of the length of respiratory tubing 42 which is proximate the patient 90 (best seen in FIG. 9). In this manner, the temperature of the aerosol upon receipt by the patient may be more accurately monitored and maintained for optimum therapeutic results. For use in its new location, the thermistor 74 is adjusted or selected to monitor temperatures in the general range of 90°-100° F.

Referring now to FIGS. 8 and 10, the lower portion 112 of the housing 102 is designed to enclose the electronic circuit, generally designated 140, which operates the heater 100. The circuitry 140 includes some of the components of the heater control circuit 80 of the heater 10, and those components will be designated with identical reference numerals.

From the exterior of the housing 102 as seen in FIG. 8, a major difference between the heater 10 and the heater 100 is that the temperature controller 81 of heater 10 has been replaced by a pair of upper and lower digital control pad switches 142, 144, respectfully. The pads 142, 144 are used to adjust the temperature of the aerosol reaching the patient, which is displayed on the digital temperature display 70.

Referring now to FIG. 10, a schematic representation is provided of the heater control circuit 140 used in the lower portion 112 of the housing 102 to operate the heater 100. The circuit 140 includes several components which are also found in the circuit 80 of the heater 10, namely the power switch 62, the power indicator light 64 (best seen in FIG. 8), the heater indicator light 66, the latter two preferably being L.E.D.'s, the safety switch 76, the power plug 82, the thermal fuse 83, and the first thermistor 74. The circuit 140 further includes the "braided" coil 124 and the second thermistor 130.

More specifically, the power plug 82 is connected to a typical 120 VAC or 220 VAC power line from a wall socket and provides power through the thermal fuse 83, a circuit breaker 146 and the safety switch 76. The power switch 62 controls the flow of power to a transformer 148 which provides isolation from the power line and reduces the voltage to a lower level which is then rectified by a bridge 150. The rectified voltage is filtered and regulated by a voltage regulator 152 and its associated capacitors 154 and 156.

A major component of the circuit 140 is a microprocessor 158 which includes a 4 MHz crystal 160, and requires four inputs to perform its temperature controlling operation. The preferred microprocessor is sold by Microchip, Inc., Chandler, Ariz., under Part No. PIC16C55.

Input to the microprocessor 158 is provided in part by the first and second thermistors, 74 and 130 respectively, which along with a 10.0K, 1% reference resistor 162 and a 0.1 μfd capacitor 164 allow the microprocessor to sense both the temperature of the coil 124 as well as the final aerosol temperature measured proximate to the patient 90. The thermistors 74, 130 act like variable resistors, and the sensed temperature values are obtained by the microprocessor comparing the rates of charging the capacitor 164 of each of the thermistors with the rate of charging required by the reference resistor 162. The microprocessor 158 then uses a translation routine to translate the capacitor charging rate readings into temperatures.

The digital pad switches 142, 144 provide the remaining two inputs to the microprocessor, and allow the operator to change the target temperature of the aerosol received by the patient as sensed by the thermistor 74, and also indicated by the display 70. The microprocessor 158 is programmed to periodically scan the switches 142, 144 to determine whether a change in target temperature is being made.

Outputs of the microprocessor 158 include a piezoelectric beeper 166 which emits two levels of audible alarm, a first low volume steady alarm when the measured temperature at the patient falls a specified amount from the target temperature, and a louder, pulsing alarm when the measured temperature rises a specified amount above the target temperature. In the preferred embodiment, the specified range of alarm-inducing temperatures is approximately ±4° of the target temperature.

Another output of the microprocessor 158 is the L.E.D. 66, which displays a visual "temperature out of range" alarm when the specified range either side of the target temperature is exceeded. A further output is the L.E.D. display, generally indicated at 70, which preferably includes display modules 168 and 170, having a corresponding drive circuitry. The drive circuitry includes a pair of 1K resistors 172 and 174, seven 510K resistors designated 176 *a-g* and a pair of N-P-N transistors 178, 180.

The final output of the microprocessor 158 is the control signal that turns on the coil 124. This output includes an optocoupler 182, preferably of the type sold by Motorola, Inc., Schaumburg, Ill., as Part No. MOC3043, and an optically coupled triac 184, which is preferably of the type sold by Texas Instruments, Dallas, Tex. as Part No. TIC2530. The triac 184 is in series with the heater coil 124. The use of the optocoupler 182 in conjunction with the transformer 148 used for power supply creates an isolation barrier which protects the microprocessor 158 and the thermistors 74, 130 from being potential shock hazards.

In operation, once the circuit 140 is installed into the lower portion 112 of the housing 102 and connected to the heater coil 124, the end plates 108, 120 are secured over the open end 106 with threaded fasteners (not shown) or other releasable fastening devices as are known in the art. The interior of the upper portion 110 of the housing is coated with silicone or other durable, heat resistant sealant to prevent the leakage of moisture into the lower portion 112.

Once assembled and connected to the nebulizer 12 as described above in relation to the heater 10, the heater 100 operates in the following manner. The power switch 62 is turned on, which causes the display 70 to flash, requesting the operator to select a target temperature. This task is accomplished through the use of the upper and lower pad switches 142, 144. Once set, the displayed temperature ceases flashing and remains constantly on.

At the same time, the microprocessor 158 sends current to the coil 124 to allow it to heat up. While this initial heating proceeds, the microprocessor 158, through the thermistor 130, monitors the rate at which the coil 124 is heating up in ° F/msec. If this rate exceeds a specified maximum rate, the power to the coil 124 is cut off until the coil cools somewhat, after which time the coil is reheated. In this manner, unwanted spiking of the heater coil 124 is prevented.

Once the heater coil 124 generates sufficient heat to be received by the patient 90, the thermistor 74 begins monitoring of the aerosol temperature at this location. Ideally, the aerosol temperature near the patient should remain relatively constant at the target temperature. However several variables, including the temperature of the room, the length of the connector tube 42, the amount of moisture in the aerosol, among other things, combine to effect the aerosol temperature perceived by the patient, either by raising or lowering the temperature. Conventional aerosol heating devices either turn on or shut off the heating coil, which often leads to relatively large variations in aerosol temperature.

To avoid such overheating or underheating, the present microprocessor 158 slows the heating/cooling cycle time and monitors, through the thermistors 74 and 130, respectively, both the patient's aerosol temperature, as well as the coil temperature. Sixteen set points are included in the microprocessor 158, and these are assigned temperature values which are relatively equally spaced between a base set point of 100° F. and a maximum set point of 250° F. The microprocessor 158 checks the thermistor 74 for a temperature reading. If the temperature is too cold, the coil is set at the highest point, e.g. 250°, and remains at that setting until the thermistor 74 reads the target temperature, such as 98° F. At that point, the heater coil 124 is then set at the base set point of 100° F. to cool until the temperature drops below the target temperature.

The microprocessor 158 then remonitors the thermistor 74, and gradually brackets in the target temperature between progressively closer set points, i.e., 110° F. for the base set point, and 240° F. as a maximum set point, then 120° F. for the base set point and 210° F. for the maximum, etc., to maintain a fairly constant target temperature reading with minimum temperature fluctuation of the heater coil 124. In this manner, spiking, overheating or underheating are prevented.

As a safety feature for the heater 100, should the monitored temperature at the patient exceed a specified safety range of, for example, 4 degrees either side of the target temperature, a protective measure is automatically taken. If the temperature is excessively above the target temperature, the power to the coil 124 is temporarily shut off by the microprocessor until the monitored temperature decreases to the target temperature. At that time, the heater coil will be turned back on.

On the contrary, if the monitored temperature falls excessively below the target temperature, the microprocessor 158 is programmed to reset the cycle as if the heater 100 had just been turned on. In other words, the heater initially heats up to a maximum temperature of 250° F., then cools down to a base temperature of 100° F., etc.

Another safety feature of the heater 100 is the provision of the audible piezoelectric beeper alarm 166. If the sensed temperature falls below the specified lower limit, a mild audible alarm signal is emitted. However, if the sensed temperature rises above the specified upper limit, the alarm 166 emits a more aggressive audible alarm signal.

Yet another feature of the present heater 100 is that when the target temperature requires changing, the operator will push the appropriate switching pad 142, 144 to reset. Upon the initial actuation of the pad 142 or 144, the display 70 begins flashing and will remain flashing for approximately two seconds. At the expiration of the two second interval, the display 70 will revert to the temperature sensed by the thermistor 74.

Accordingly, the nebulizer heater of the invention accurately and safely provides a heated aerosol to a respiratory patient by heating the aerosol subsequent to its nebulization. A control system monitors the heated aerosol and controls the heater accordingly to maintain the aerosol within specified temperature parameters. A temperature sensor is located proximate to the point at which the patient receives the aerosol to ensure that the patient receives properly heated aerosol. The sensor provides feedback signals to the temperature control system, which adjusts the temperature of the heater coil to prevent spiking, underheating or overheating of the aerosol.

While particular embodiments of the aerosol nebulizer heater of the invention have been shown and described, it will be appreciated by those skilled in the art that changes and modifications may be made thereto without departing from the invention in its broader aspects and as set forth in the following claims.

What is claimed is:

1. A heater for use with a respiratory nebulizer producing a pressurized aerosol, comprising:

a housing having an inlet end and an outlet end, each of said ends having a respective port, said inlet end port and said outlet end port being in fluid communication with each other;

said inlet end port being configured for fluid communication with the nebulizer so as to receive the aerosol upon connection of said housing to the nebulizer; and means for heating the aerosol as the aerosol passes through said housing and out said outlet end port, said means for heating including a tubular heating chamber having a tubular heating element with multiple heated surfaces disposed in said chamber so that aerosol passing through said chamber directly contacts said heated surfaces.

2. The heater as defined in claim 1 wherein said means for heating includes a tubular coil.

3. The heater as defined in claim 2 wherein said coil is made of a plurality of windings of different diameters which create multiple openings for the flow of aerosol therethrough.

4. The heater as defined in claim 3 further including an insulating barrel surrounding said coil to define said heating chamber.

5. The heater as defined in claim 4 wherein said coil is frictionally engaged in said insulating barrel.

6. The heater as defined in claim 1 further including control means for controlling the flow of current from an electrical power source to said tubular heating element.

7. The heater as defined in claim 6 wherein said control means includes a thermostat for monitoring the temperature of said heating element.

8. The heater as defined in claim 6 wherein the control means further includes sensing means for sensing the temperature of said heating element.

9. The heater as defined in claim 8 further including outlet end port sensing means for sensing the temperature of heated aerosol emitted from said outlet end port, said outlet end port sensing means being connected to said control means.

10. The heater as defined in claim 9 wherein said outlet end port sensing means is disposed in a connecting tube proximate to a point at which the patient receives the aerosol.

11. The heater as defined in claim 9 wherein said outlet end port sensing means is a thermistor.

12. The heater as defined in claim 6 further including a safety switch disposed on said housing to control the flow of electrical current passing to said heating element.

13. The heater as defined in claim 6 further including indicating means for indicating when said heating element is heating the aerosol.

14. The heater as defined in claim 6 wherein said control means is configured to adjust the amount of heat emitted by the heating element in response to signals generated by temperature sensing means located proximate to the patient.

15. The heater as defined in claim 14 wherein said control means is further configured to repeatedly monitor said temperature sensing means and to bracket the amount of heat generated by the heating element between progressively closer base and maximum temperatures.

16. The heater as defined in claim 1 wherein said housing includes a locating formation for securely and accurately positioning said heater upon the nebulizer.

17. A heater for use with a respiratory nebulizer producing a pressurized aerosol, comprising:

a housing having an inlet end and an outlet end, each of said ends having a respective port, said inlet end port and said outlet end port being in fluid communication with each other;

said inlet end port being configured for fluid communication with the nebulizer so as to receive the aerosol upon connection of said housing to the nebulizer;

means located in said housing for heating the aerosol as the aerosol passes through said housing and out said outlet end port, said means for heating including an insulator barrel defining a tubular heating chamber having a tubular heating element with multiple heated surfaces, said heating element being disposed in said chamber so that aerosol passing through said chamber directly contacts said heated surfaces; and means for monitoring and controlling the temperature of the aerosol as it passes through said housing and out said outlet end port, said monitoring means including first sensing means located to monitor the temperature of said heating element and second sensing means positioned to monitor the temperature of aerosol heated by said heating element and emitted from said outlet end port.

18. The heater as defined in claim 17 wherein said means for heating includes an electrically heated coil frictionally engaged within said insulator barrel.

19. The heater as defined in claim 17 further including a safety switch disposed on said housing to ensure proper connection with between said heating element and the nebulizer prior to energization of said means for heating.

20. The heater as defined in claim 17 wherein said means for monitoring and controlling is configured to receive signals from said first and second temperature sensing means and to control the heating of said heating element accordingly so that the patient receives aerosol heated at a constant target temperature.

21. The heater as defined in claim 17 wherein said control means is further configured to repeatedly monitor said temperature sensing means and to bracket the amount of heat generated by the heating element between progressively closer base and maximum temperatures.

22. The heater as defined in claim 17 further including visual temperature indicating means for indicating the temperature of said aerosol sensed by said second sensing means.

23. The heater as defined in claim 17 wherein said first sensing means includes a thermistor located in operational proximity to said heating element, and said second sensing means is another thermistor located in operational proximity to a connector tube to monitor the temperature of the heated aerosol proximate the patient.

24. The heater as defined in claim 17 further including warning means for indicating where the temperature served by said sensing means is outside specified limits.

* * * * *